United States Patent [19]

Carter et al.

[11] Patent Number: 5,912,741
[45] Date of Patent: Jun. 15, 1999

[54] IMAGING SCATTEROMETER

[75] Inventors: Ron R. Carter, Whittier; Larry K. Pleskot, Yorba Linda, both of Calif.

[73] Assignee: Northrop Grumman Corporation, Los Angeles, Calif.

[21] Appl. No.: 08/962,946

[22] Filed: Oct. 10, 1997

[51] Int. Cl.[6] ............................ G01N 21/55; G01N 21/47
[52] U.S. Cl. ................................... 356/445; 356/446
[58] Field of Search ................................ 356/445, 446, 356/236

[56] References Cited

U.S. PATENT DOCUMENTS

| | | | |
|---|---|---|---|
| 1,979,952 | 11/1934 | Benford | 88/23 |
| 4,360,275 | 11/1982 | Louderback | 356/446 |
| 4,412,746 | 11/1983 | Yokouchi | 356/446 |
| 4,547,073 | 10/1985 | Kugimiya | 356/371 |
| 4,555,635 | 11/1985 | Yoshida | 250/572 |
| 4,673,818 | 6/1987 | Guerra | 250/571 |
| 4,815,858 | 3/1989 | Snail | 356/446 |
| 4,859,062 | 8/1989 | Thurn et al. | 356/371 |
| 4,954,722 | 9/1990 | Fine et al. | 250/571 |
| 4,988,205 | 1/1991 | Snail | 356/446 |
| 5,196,906 | 3/1993 | Stover et al. | 356/446 |
| 5,241,369 | 8/1993 | McNeil et al. | 356/445 |
| 5,637,873 | 6/1997 | Davis et al. | 356/446 |

*Primary Examiner*—Robert H. Kim
*Assistant Examiner*—Amanda Merlino
*Attorney, Agent, or Firm*—Terry J. Anderson; Karl J. Hoch, Jr.

[57] ABSTRACT

A scatterometer for providing measurements of the directional energy distribution of radiation reflected from the surface of a sample material as two-dimensional images, the images being representative of surface characteristics of the sample material, as viewed from different directions, without moving the sample material being examined, is disclosed. The scatterometer comprises a radiation source, a first reflector, a second reflector, a detector and a beam steerer.

36 Claims, 2 Drawing Sheets

IMAGING SCATTEROMETER

FIELD OF THE INVENTION

The present invention relates generally to optical measurement devices and more particularly to an imaging scatterometer for measuring and representing the directional energy distribution of radiation reflected from a sample surface or volume as a two-dimensional image to provide characterization of the microstructure of the sample such as optical performance information, surface roughness statistics, defect characteristics, etc.

BACKGROUND OF THE INVENTION

By measuring the directional energy distribution of radiation reflected from a sample surface, scatterometers provide a simple and noncontact monitoring technique to determine the surface and sub-surface microstructure of the sample. For example, if the sample surface is perfectly mat then the reflected radiation is diffuse, i.e., equal in all directions, while if the sample surface is not perfectly mat then the reflected radiation is specular, i.e., more concentrated in certain directions. This technique is useful in many areas of technology, such as fabrication of microelectronics materials, fabrication of optoelectronics materials and manufacturing of computer disks, where it is important to determine whether there is any defect in a sample material. Moreover, since this technique is noncontact, it allows measurements to be made in-situ to assist the quality control of manufacturing processes used in these areas of technology.

An existing problem in the field of scatterometry is the lack of optical systems which can provide accurate measurements of both diffuse and specular reflectance, control of the angle of incidence of the radiation beam directed upon the sample surface, and simultaneous measurements of all radiation reflected from the sample surface to represent the directional reflectance distribution as a two-dimensional image. Certain prior art scatterometers have some, but not all, of the above desired features.

For example, a prior art scatterometer, described in U.S. Pat. No. 5,241,369, employs a screen positioned to receive and display a pattern representative of light specularly reflected and scattered from an illuminated sample and a camera to record the pattern displayed on the screen. The use of the screen results in a re-illumination of the sample by reflections from the screen, corrupting the measurements. Consequently, accurate measurements of reflectance distribution are not possible with this prior art scatterometer.

Another prior art scatterometer, described in U.S. Pat. No. 4,988,205, comprising a primary mirror, a secondary mirror, a radiation source and a radiation detector, provides accurate measurements of only total diffuse reflectance. This prior art scatterometer does not provide measurements of directional reflectance. Moreover, the angle of incidence of the radiation beam directed upon the sample surface is fixed and cannot be regulated during the operation of this prior art scatterometer.

SUMMARY OF THE INVENTION

The present invention specifically addresses all of the above mentioned desired features. The present invention provides measurements of the directional energy distribution of radiation reflected from the surface of a sample material as two-dimensional images, the images being representative of surface characteristics of the sample material, as viewed from different directions, without moving the sample material being examined.

More particularly, the present invention comprises a radiation source, a first reflector, a second reflector, a detector and a beam steerer. The radiation source produces a radiation beam which is directed along an optical path from the source of radiation to a selected point on the surface of the sample material. The first reflector is located along the optical path. The surface of the first reflector is impacted by the radiation beam at a first incident point. The first reflector reflects the radiation beam to the second reflector which is located along the optical path, downstream from the first reflector. The second reflector focuses the reflected radiation beam onto the selected point on the surface of the sample material at an angle of incidence. This angle of incidence is determined by the location of the first incident point on the surface of the first reflector. The sample material reflects the focused radiation beam as a plurality of reflected radiation rays which are captured by the detector. The beam steerer located along the optical path, between the radiation source and the first reflector, varies the location of the first incident point along the surface of the first reflector, thereby indirectly regulates the angle of incidence of the focused radiation beam incident upon the surface of the sample material, so as to facilitate reflectance measurements at different values of this angle of incidence.

In the first embodiment of the invention, the imaging scatterometer comprises a radiation source, a first reflector of convex dome-shaped configuration, a second reflector of ellipsoidal shape, a detector and a beam steerer. The radiation source provides a radiation beam. The beam steerer optically processes the radiation beam to control the location of the first incident point at which the radiation beam strikes the surface of the first reflector. The first reflector reflects the radiation beam to the second reflector which then focuses it onto a selected point on the surface of a sample material. The focused radiation beam striking the surface of the sample material at an angle of incidence is reflected by the sample material, either specularly or diffusely, as a plurality of reflected radiation rays, onto the second reflector. The second reflector focuses the reflected radiation rays to the first reflector which then reflects the focused radiation rays to a detector. By controlling the location of the first incident point at which the radiation beam strikes the surface of the first reflector, the beam steerer indirectly controls the angle of incidence of the focused radiation beam which strikes the surface of the sample material. Thus, measurements of radiation reflected from the sample material, either specularly or diffusely, in response to a radiation beam incident upon the sample material at any angle of incidence, are possible with the present invention. In addition, the present invention allows measurements of reflected radiation rays which lie outside the plane of incidence which is defined as the plane comprising the radiation beam incident upon the selected point on the surface of the sample material and the normal to the surface of the sample material at that point. This feature is a significant improvement over many current scatterometers which use mechanical means to position the radiation source and the detector relative to the sample material surface. Most of these devices can only measure the reflected rays that lie in the plane of incidence.

A second embodiment of the invention comprises a radiation source, a first reflector of concave dome-shaped configuration, a second reflector of ellipsoidal shape, a detector and a beam steerer. The only difference between this embodiment and the first embodiment of the invention is that the shape of the first reflector is concave instead of convex. The functionality of this second embodiment is similar to that of the first embodiment. The radiation source provides a radiation beam. The beam steerer optically processes the radiation beam to control the location of the first incident point at which the radiation beam strikes the first reflector. The first reflector reflects the radiation beam to the second reflector which then focuses it onto a selected point on the surface of a sample material. The focused radiation beam striking the surface of the sample material at an angle of incidence is thereafter reflected by the sample material, either specularly or diffusely, as a plurality of reflected radiation rays, onto the second reflector. The second reflector focuses the reflected radiation rays to the first reflector which then reflects the focused radiation rays to a detector.

A third embodiment of the invention comprises a radiation source, a detector and an optical train. The radiation source provides a radiation beam which is directed onto a sample material surface. The optical train collects $2\pi$ steradians of radiation reflected from the sample material surface and focuses the reflected radiation rays onto the detector. The detector transforms the reflected radiation rays into a two-dimensional image.

A fourth embodiment of the invention comprises a radiation source, a first reflector of flat mirrored configuration, a second reflector of oblate ellipsoidal shape, a detector and a beam steerer. The ratio of the axes of the oblate ellipsoidal second reflector and the location of the flat mirrored first reflector result in the first focal point of the second reflector being a virtual image of an aperture, the aperture being located on the second reflector, the virtual image facing the non-reflective surface of the first reflector. The first and second reflectors have the same perimeter and are connected together to form an enclosure. The sample material is disposed at the second focal point of the second reflector, makes contact with the back of the first reflector and can be illuminated through an aperture in the first reflector. The radiation source provides a radiation beam. The beam steerer optically processes the radiation beam to control the location of the first incident point at which the radiation beam strikes the first reflector. The first reflector reflects the radiation beam to the second reflector which then focuses it onto a selected point on the surface of a sample material. The focused radiation beam striking the surface of the sample material at an angle of incidence is thereafter reflected by the sample material, either specularly or diffusely, as a plurality of reflected radiation rays, onto the second reflector. The second reflector focuses the reflected radiation rays to the first focal point. The first reflector intercepts the focused radiation rays then reflects them to a detector. The detector transforms the reflected radiation rays into a two-dimensional image.

DETAILED DESCRIPTION OF THE INVENTION

The detailed description set forth below in connection with the appended drawings is intended as a description of the presently preferred embodiments of the invention, and is not intended to represent the only forms in which the present invention may be constructed or utilized. The description sets forth the functions and the sequence of the steps for constructing and operating the invention in connection with the illustrated embodiments. It is to be understood, however, that the same or equivalent functions may be accomplished by different embodiments that are also intended to be encompassed within the spirit and scope of the invention.

Figure 1:
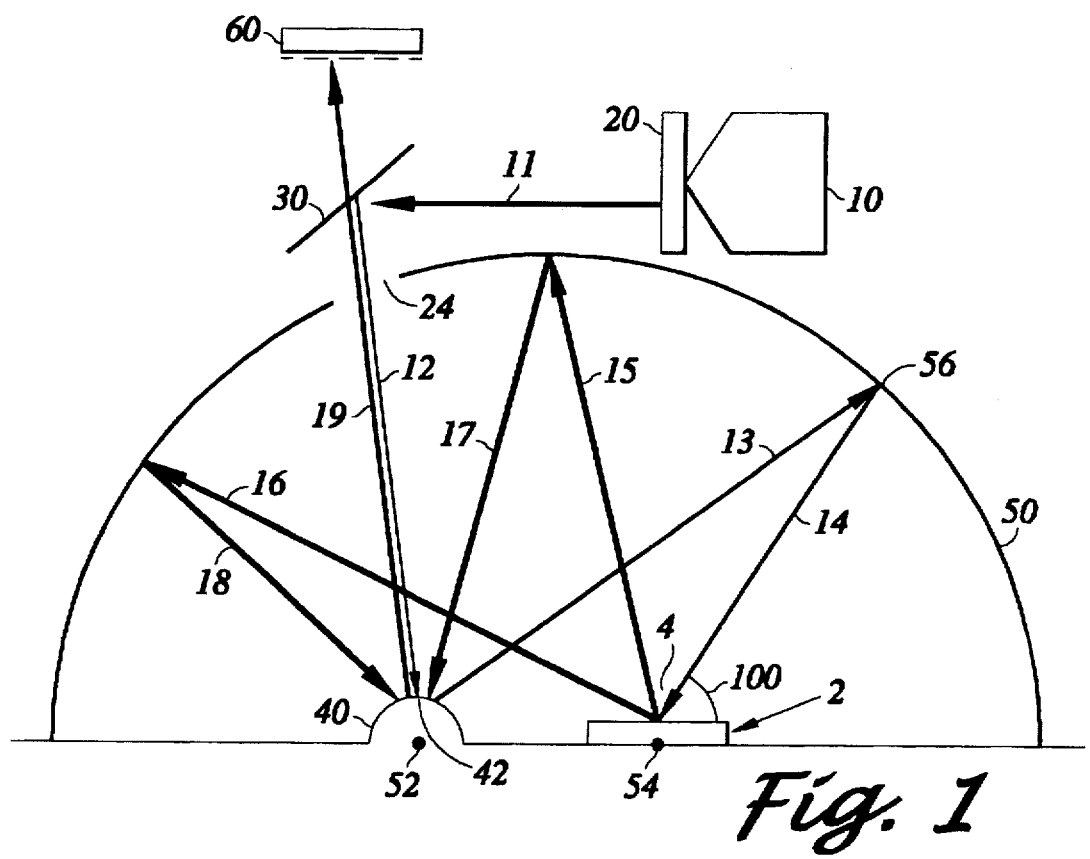
FIG. 1 is a schematic diagram of a preferred embodiment of the present invention including a convex dome-shaped reflector and a concave prolate ellipsoidal reflector.

The imaging scatterometer of the present invention is illustrated in FIG. 1 which depicts a presently preferred embodiment of the invention. The imaging scatterometer is comprised primarily of a concave prolate ellipsoidal reflector 50 having two focal points 52 and 54, inside the cavity of which reside a convex dome-shaped reflector 40 situated about the first focal point 52 and a sample material 2 situated about the second focal point 54. The concave prolate ellipsoidal reflector 50 contains an aperture 24 opposite the convex dome-shaped reflector 40. This preferred embodiment of the invention further comprises a beam steerer 20, a beam splitter 30, and an imaging detector 60, all of which reside outside the cavity of the concave prolate ellipsoidal reflector 50.

In the typical operation of the preferred embodiment, a collimated beam of radiation 10 passes through the beam steerer 20 which controls the position and angle of the emerging radiation beam 11. Thereafter, the radiation beam 11 is redirected as radiation beam 12 to the aperture 24 by means of a beam splitter 30. Inside the cavity of the ellipsoidal reflector 50, the radiation beam 12 strikes the convex dome-shaped reflector 40 at the incident point 42 and thereafter is reflected as radiation beam 13 toward the interior surface of the ellipsoidal reflector 50 which in turn reflects and focuses the radiation beam 13 as radiation beam 14 onto a selected point 4 on the sample material 2.

The collimated radiation beam 10 may be an optical energy of any chosen wavelength or wavelengths, or an electromagnetic energy of any chosen wavelength or wavelengths, as long as the energy wavelength is within the operating range of the imaging scatterometer.

The beam steerer 20 optically processes the collimated radiation beam 10 and outputs the collimated beam of radiation 11 of a desired position and angle. An example of a beam steerer is a spatial light modulator which can be used as a light beam deflector. Currently, spatial light modulators are used in two applications: wavefront phase modulation and spatial intensity modulation. The type of spatial light modulator suitable for use in conjunction with the present invention is the one used for spatial intensity modulation. It can be of transmissive or reflective type. The reflective type either modulates the spatial reflectance or controls an array of micro-mirrors to redirect the incident radiation beam.

The radiation beam 11 strikes the beam splitter 30 which redirects radiation beam 11 as radiation beam 12 to the convex dome-shaped reflector 40 with a small loss of radiation beam 11 intensity level but without any loss of its spatial information. The spatial information in the cross section of radiation beam 11 represents a particular directional distribution of energy. For example, if the spatial light modulator 20 outputs radiation beam 11 as a map of a real or simulated radiative scene, then the spatial information in the cross section of radiation beam 11 represents the directional distribution of energy of that scene. The location 42 at which beam 12 strikes the reflector 40 depends on the position and angle of beam 11, which are controlled by the beam steerer 20.

Reflector 40 is a rotationally symmetric convex dome having an exterior reflective surface which enables it to reflect virtually all of the collimated radiation beam 12 to the ellipsoidal reflector 50 as the radiation beam 13.

Ellipsoidal reflector 50 collects virtually all of the radiation beam 13 at location 56 and, because of its reflective interior surface and its concave ellipsoidal curvature, focuses radiation beam 13 as radiation beam 14 to its second focal point 54 about which the sample material 2 is located. It is well known that an ellipsoidal reflector collects radiation rays reflected from one of its two focal points and focuses these radiation rays to the other focal point. Focusing properties of ellipsoidal reflectors are addressed in a paper entitled "Focusing Properties of Hemispherical and Ellipsoidal Mirror Reflectometers", W. M. Brandenberg, Journal of Optical Society of America, Vol. 54, No. 12, pp. 1235–1237, October 1964.

Radiation beam 14 strikes the surface of the sample material 2 at point 4, at an angle of incidence 100. The value of the angle of incidence 100 is determined by the location of the incident point 42 at which radiation beam 12 strikes reflector 40. Due to the curved surface of reflector 40, a small variation in the location of the incident point 42 corresponds to a large variation in the location 56 where radiation beam 13 strikes reflector 50. This variation in the location 56 translates into a significant change in the angle of incidence 100. If the sample material 2 is very thin, as all microelectronics and optoelectronics materials are, then point 4, where radiation beam 14 strikes the sample material surface, remains virtually unchanged since it is right above the focal point 54 to which radiation beam 14 is focused. Thus, by controlling the location of the incident point 42 at which radiation beam 12 strikes the reflector 40, the angle of incidence 100 can be regulated. If sample material 2 is of greater thickness, sample material 2 can be moved downward so that point 4 coincides with the focal point 54. Thus, this scatterometer could be made portable to be used in characterizing the surface reflectance of a large object.

Sample material 2 reflects radiation beam 14 either specularly or diffusely, depending on the microstructure of its surface, resulting in a plurality of radiation rays striking the interior surface of the ellipsoidal reflector 50 at various points located within the boundaries of reflector 50. These various radiation rays are illustrated by only two radiation rays 15, 16. Due to the focusing properties of ellipsoidal reflector 50 as mentioned above, these various radiation rays are redirected to the first focal point 52 of reflector 50, about which the convex dome-shaped reflector 40 is located. The directional incident energy distribution at the first focal point 52 is the inverse of the scattering energy distribution at the second focal point 54. Reflector 40 narrows the angular spread of all the radiation rays incident upon its exterior surface and reflects virtually all of them toward the aperture 24 in the form of a collimated beam of radiation 19 comprising a multitude of parallel or nearly parallel radiation rays. Aperture 24 is sufficiently large to allow the passage of the collimated beam 19, but small enough so that its effect on the focusing properties of the reflector 50 is negligible.

The collimated radiation beam 19 passes through the beam splitter 30 retaining its spatial information, though losing some of its intensity level. The spatial information of the collimated radiation beam 19 represents the directional energy distribution of the radiation rays incident upon reflector 40. The imaging detector 60 captures the radiation beam 19 after it emerges from the beam splitter and transforms it into a two-dimensional digital image, each pixel of which corresponds to a single ray in the collimated beam 19. A focal plane array can be used as the imaging detector 60.

The following discussion on focal plane arrays, though not crucial to the invention, explains how the focal plane array 60 captures simultaneous measurements of all radiation rays reflected from the sample material surface. Commercially available focal plane arrays comprise mainly of three parts: a camera head, digital electronics and software. Current focal plane array technology allows transformation of a radiation beam comprising a multitude of radiation rays into a 512×512 digital image, i.e., a square image having $(512)^2$ pixels. In the present invention, since the radiation beam 19 is imaged as a circular section, only $\pi/4$ of the available pixels are used, i.e., about 200,000 pixels. Since each pixel represents the measurement of a single radiation ray impacting reflector 50 due to the reflectance of the surface of sample material 2, the output image of the focal plane array 60 represents about 200,000 distinct measurements taken simultaneously. The resolution of these measurements is 180 degrees/512=0.35 degrees. Current focal plane array technology provides 12-bit images at a rate greater than the 30 Hz video rate. This dynamic range is acceptable for many applications. The spatial light modulator 20 can also output radiation beam 11 as a map of a real or simulated radiative scene. In such a case, the output image of the focal plane array 60 represents the reflectance distribution function of the sample material 2 in response to such a scene.

Figure 2:
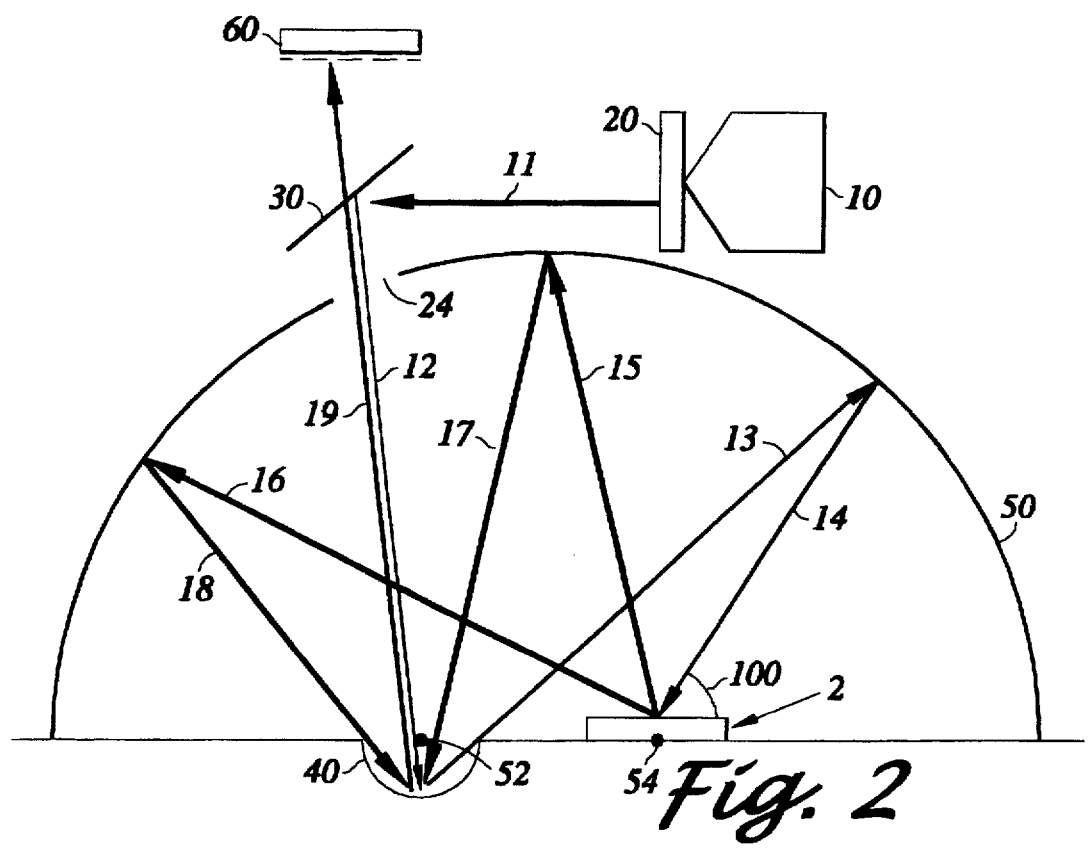
FIG. 2 is a schematic diagram of a second embodiment of the present invention. The only difference between this embodiment and the first embodiment of the invention is that the shape of the first reflector in this embodiment is concave instead of convex.

A second embodiment of the invention is depicted in FIG. 2. This embodiment differs from the one previously discussed by comprising as reflector 40 a concave dome-shaped reflector having reflective interior surface. The functionality of this second embodiment is similar to the previous one.

In the second embodiment, a collimated beam of radiation 10 passes through the beam steerer 20 which controls the position and angle of the emerging radiation beam 11. Thereafter, the radiation beam 11 is directed to the aperture 24 by means of a beam splitter 30. Inside the cavity of the prolate ellipsoidal reflector 50 the radiation beam is reflected by the concave dome-shaped reflector 40 and directed toward the interior surface of the prolate ellipsoidal reflector 50 which in turn reflects and focuses the radiation beam onto a selected point 4 on the sample material 2.

The beam steerer 20 optically processes the collimated radiation beam 10 and outputs the collimated beam of radiation 11 of a desired position and angle. A spatial light modulator may be used as a beam steerer.

The radiation beam 11 strikes the beam splitter 30 which redirects radiation beam 11 as radiation beam 12 to the concave dome-shaped reflector 40 with a small loss of radiation beam 11 intensity level but without any loss of its spatial information. The location 42 at which beam 12 impacts the reflector 40 depends on the position and angle of beam 11, which are controlled by the beam steerer 20.

Reflector 40 is a rotationally symmetric concave dome having an interior reflective surface which enables it to reflect virtually all of the collimated radiation beam 12 to the ellipsoidal reflector 50 as the radiation beam 13.

Ellipsoidal reflector 50 collects virtually all of the radiation beam 13 at location 56 and, because of its reflective interior surface and its concave ellipsoidal curvature, redirects radiation beam 13 as radiation beam 14 to its second focal point 54 about which the sample material 2 is located.

Radiation beam 14 strikes the surface of the sample material 2 at point 4, at an angle of incidence 100. The value of the angle of incidence 100 is determined by the location of the incident point 42 at which radiation beam 12 strikes reflector 40. Due the curved surface of reflector 40, a small variation in the location of the incident point 42 corresponds to a large variation in the location 56 where radiation beam 13 strikes reflector 50. This variation in the location 56 translates into a significant change in the angle of incidence 100. If the sample material 2 is very thin, as all microelectronics and optoelectronics materials are, then point 4, where radiation beam 14 strikes the sample material surface, remains virtually unchanged since it is right above the focal point 54 to which radiation beam 14 is focused. Thus, by controlling the location of the incident point 42 at which radiation beam 12 strikes reflector 40, the angle of incidence 100 can be regulated. If sample material 2 is of greater thickness, sample material 2 can be moved downward so that point 4 coincides with the focal point 54. Thus, this scatterometer could be made portable to be used in characterizing the surface reflectance of a large object.

Sample material 2 reflects radiation beam 14 either specularly or diffusely, depending on the microstructure of its surface, resulting in a plurality of radiation rays striking the interior surface of the ellipsoidal reflector 50 at various points located within the boundaries of reflector 50. These various radiation rays are illustrated by only two radiation rays 15, 16. Due to the focusing properties of ellipsoidal reflector 50 as mentioned above, these various radiation rays are redirected to the first focal point 52 of reflector 50, about which the concave dome-shaped reflector 40 is located. The directional incident energy distribution at the first focal point 52 is the inverse of the scattering energy distribution at the second focal point 54. Reflector 40 narrows the angular spread of all the radiation rays incident upon its interior surface and reflects virtually all of them toward the aperture 24 in the form of a collimated beam of radiation 19 comprising a multitude of parallel or nearly parallel radiation rays. Aperture 24 is sufficiently large to allow the passage of the collimated beam 19, but small enough so that its effect on the focusing properties of the reflector 50 is negligible.

The collimated radiation beam 19 passes through the beam splitter 30 retaining its spatial information, though losing some of its intensity level. The spatial information of the collimated radiation beam 19 represents the directional energy distribution of the radiation rays incident upon reflector 40. The imaging detector 60 captures the radiation beam 19 after it emerges from the beam splitter and transforms it into a two-dimensional digital image, each pixel of which corresponds to a single ray in the collimated beam 19. A focal plane array can be used as the imaging detector 60.

Figure 3:
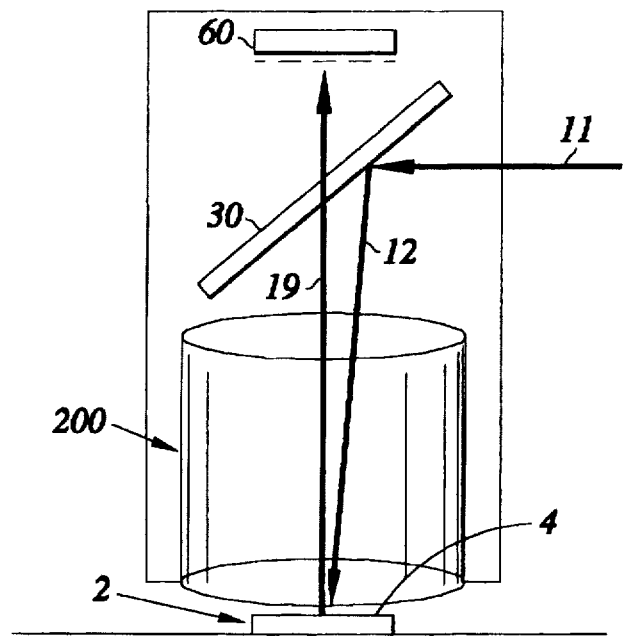
FIG. 3 is a schematic diagram of a third embodiment of the present invention including an imaging detector and an optical train for focusing $2\pi$ steradians of radiation rays reflected from a sample material surface onto the imaging detector.

A third embodiment of the invention is depicted in FIG. 3. This embodiment includes an optical train 200, a beam splitter 30 and a focal plane array 60. The collimated beam of radiation 11 is redirected by the beam splitter 30 as radiation beam 12 onto the surface of the sample material 2 at point 4. The optical train 200 collects virtually all of the radiation rays reflected from the surface of the sample material 2 and focuses $2\pi$ steradians of radiation as beam 19 onto the imaging detector 60.

Figure 4:
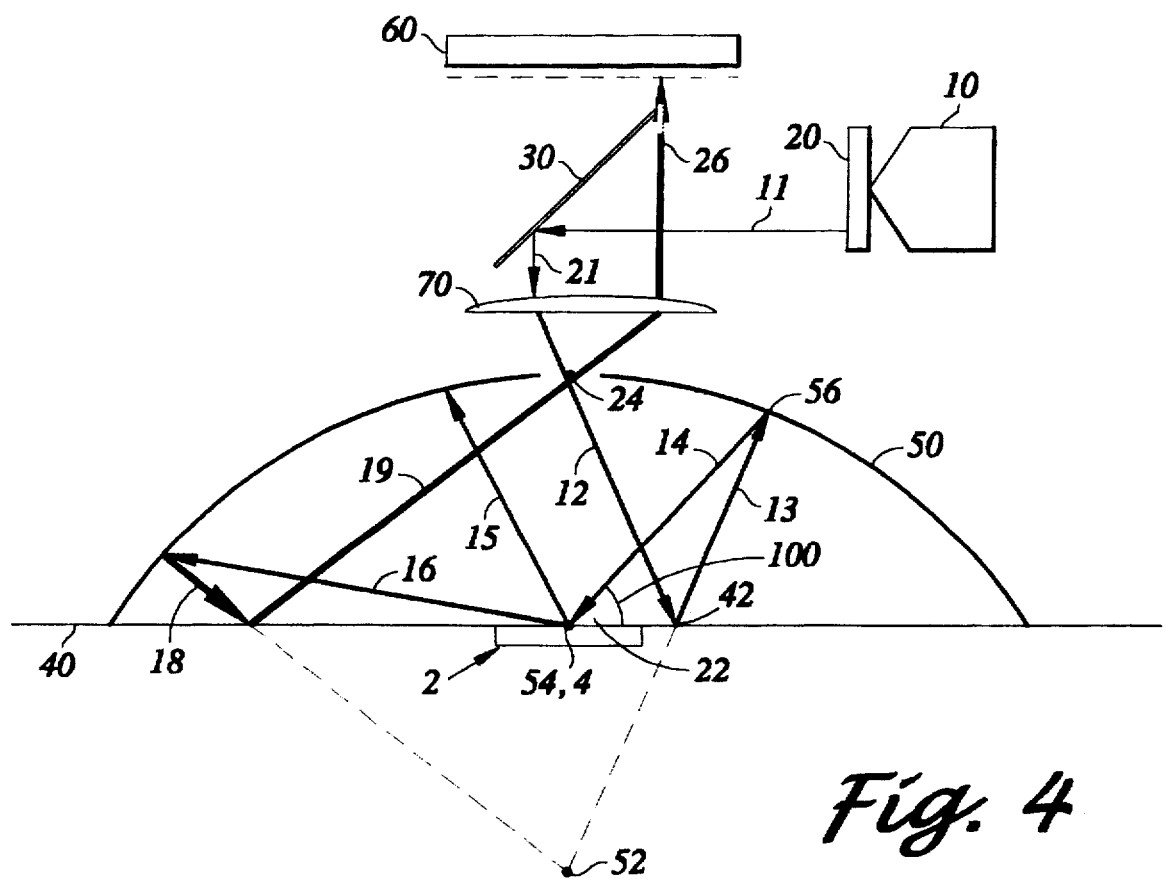
FIG. 4 is a schematic diagram of a fourth embodiment of the present invention including a flat mirrored reflector and a concave oblate ellipsoidal reflector.

A fourth embodiment of the invention is depicted in FIG. 4. Referring to FIG. 4, the imaging scatterometer is comprised primarily of two reflectors 40 and 50. Reflector 50 is a concave oblate ellipsoidal reflector having two focal points 52 and 54 located on its major axis and an aperture 24 collinear with the two focal points 52, 54. The ratio of its major axis over its minor axis is such that the distance between the two focal points 52 and 54 is equal to the distance between focal point 54 and aperture 24. In this embodiment, this ratio is 3/sqrt(8) which is aproximately equal to 1.06. Reflector 40 is a thin flat mirror having an aperture 22 located about its center. Focal point 54 is located within aperture 22. Reflector 40 is positioned inside the cavity of reflector 50 on the plane containing the focal point 54 and orthogonal to the major axis of the oblate ellipsoidal reflector 50. Reflectors 40 and 50 have the same perimeter and are connected together to form an enclosure. A characteristic of a flat mirror is that, for any point at a given distance in front of the mirror, a virtual image of that point is produced at the same distance behind the mirror. Thus, due to the flat mirrored reflector 40 and due to the ratio of the axes of reflector 50, focal point 52 is a virtual image of a point located within aperture 24.

Referring to FIG. 4, the fourth embodiment further comprises a beam steerer 20, a beam splitter 30, an imaging detector 60, and a lens 70, all of which reside outside the cavity of the concave oblate ellipsoidal reflector 50. Sample material 2 makes contact with the back of reflector 40, and is disposed about focal point 54.

In the fourth embodiment, a collimated beam of radiation 10 passes through the beam steerer 20 which controls the position and angle of the emerging radiation beam 11. The beam steerer 20 optically processes the collimated radiation beam 10 and outputs the collimated beam of radiation 11 of a desired position and angle. A spatial light modulator may be used as beam steerer 20.

The radiation beam 11 strikes the beam splitter 30 which redirects radiation beam 11 as radiation beam 21 to the optical lens 70 with a small loss of radiation beam 11 intensity level but without any loss of its spatial information. Lens 70 focuses the emerging radiation beam 12 onto the reflector 40, through aperture 24. The location 42 at which beam 12 strikes the reflector 40 depends on the position and angle of beam 11, which are controlled by the beam steerer 20.

Inside the cavity of the ellipsoidal reflector 50, the radiation beam 12 is reflected by the flat mirrored reflector 40 as radiation beam 13. Radiation beam 13 will appear to emanate from the direction of focal point 52, since the flat mirrored reflector 40 produces a virtual image of the aperture 24 at focal point 52. Radiation beam 13 is intercepted by the interior surface of the ellipsoidal reflector 50 which reflects it as radiation beam 14 and focuses the radiation beam 14 onto a selected point 4 on the sample material 2.

Due to its mirrored surface, reflector 40 reflects radiation beam 12 to the ellipsoidal reflector 50 as the radiation beam 13. Ellipsoidal reflector 50 collects virtually all of the radiation beam 13 at location 56 and, because of its reflective interior surface and its concave ellipsoidal curvature, redirects radiation beam 13 as radiation beam 14 to its second focal point 54 about which the sample material 2 is located.

Radiation beam 14 strikes the surface of the sample material 2 at point 4, at an angle of incidence 100. The value of the angle of incidence 100 is determined by the location of the incident point 42 at which radiation beam 12 strikes reflector 40.

Sample material 2 reflects radiation beam 14 either specularly or diffusely, depending on the microstructure of its surface, resulting in a plurality of radiation rays striking the interior surface of the ellipsoidal reflector 50 at various points located within the boundaries of reflector 50. These various radiation rays are illustrated by only two radiation rays 15, 16. Due to the focusing properties of ellipsoidal reflector 50 as mentioned above, these various radiation rays are redirected to the first focal point 52 of reflector 50. These radiation rays, illustrated in FIG. 4 by only one radiation ray 18, strike the flat mirrored reflector 40 at various points. Since focal point 52 is a virtual image of a point in aperture 24 as discussed above, the radiation rays converging towards focal point 52 are reflected off the flat mirrored reflector 40 and redirected towards aperture 24. In FIG. 4, these redirected radiation rays are illustrated by only one radiation ray 19. The angular spread of all these radiation rays as they pass through aperture 24 is approximately 53 degrees from the center ray which is collinear with the major axis of the reflector 50. Aperture 24 is sufficiently large to allow passage of all of these radiation rays. Optical lens 70 provides corrections to the aberrations caused by reflector 50 and focuses these radiation rays onto the imaging detector 60 as collimated radiation beam 26. The radiation beam 26, emerging from lens 70 and passing through beam splitter 30, retains the spatial information representing the directional energy distribution of the radiation reflected from sample material 2. The imaging detector 60 captures the radiation beam 26 after it emerges from the beam splitter 30 and transforms it into a two-dimensional digital image. A focal plane array can be used as the imaging detector 60.

It is understood that the exemplary scatterometers described herein and shown in the drawings represent only presently preferred embodiments of the invention. Indeed, various modifications and additions may be made to such embodiments without departing from the spirit and scope of the invention. For example, the reflectors and the detector need not be configured as illustrated. Also, the radiation source need not be a source of visible light. Those skilled in the art will recognize that various other physical or optical configurations are equivalent and therefore likewise suitable. Thus, these and other modifications and additions may be obvious to those skilled in the art and may be implemented to adapt the present invention for use in a variety of different applications.

What is claimed is:

1. A method for measuring directional energy distribution of radiation reflected from a surface of a sample material with a stationary imaging receiver system, received images being representative of surface characteristics of the sample material, as viewed from a plurality of different directions, without moving the sample material being examined, the method comprising the steps of:

(a) directing a radiation beam from a source of radiation onto a first incident point on a surface of a first reflector;

(b) reflecting the radiation beam from the first reflector to a second reflector;

(c) focusing the radiation beam from the second reflector onto a first point on the surface of the sample material at an angle of incidence, whereupon the sample material reflects the focused radiation beam as a plurality of reflected radiation rays impacting the second reflector;

(d) regulating the angle of incidence by varying the location of the first incident point along the surface of the first reflector so as to facilitate reflectance measurements at different values of the angle of incidence; and (e) measuring the reflected radiation rays.

2. The method as recited in claim 1 wherein step (a) comprises directing a light beam from a source of light.

3. The method as recited in claim 1 wherein step (a) comprises directing a visible light beam from a source of visible light.

4. The method as recited in claim 1 wherein step (a) comprises the step of directing a radiation beam through a beam steerer to vary the location of the first incident point along the surface of the first reflector.

5. The method as recited in claim 1 wherein step (a) comprises the step of directing a radiation beam through a spatial light modulator to vary the location of the first incident point along the surface of the first reflector.

6. The method as recited in claim 1 wherein step (a) comprises the step of directing a radiation beam through a beam splitter and a beam steerer to vary the location of the first incident point along the surface of the first reflector.

7. The method as recited in claim 1 wherein step (a) comprises the step of directing a radiation beam through a beam splitter and a spatial light modulator to vary the location of the first incident point along the surface of the first reflector.

8. The method as recited in claim 1 wherein step (a) comprises directing a collimated radiation beam from a source of collimated radiation.

9. The method as recited in claim 1 further comprising the steps of:

(1) focusing the reflected radiation rays from the second reflector to the first reflector; and (2) reflecting the focused radiation rays from the first reflector to a detector.

10. The method as recited in claim 1 further comprising the steps of:

(1) focusing the reflected radiation rays from the second reflector to a virtual point, the virtual point facing a non-reflective surface of the first reflector;

(2) intercepting the reflected radiation rays with the first reflector; and (3) reflecting the intercepted radiation rays from the first reflector to a detector.

11. The method as recited in claim 1 wherein the second reflector is concave prolate ellipsoidal.

12. The method as recited in claim 1 wherein the second reflector is concave oblate ellipsoidal.

13. The method as recited in claim 1 wherein the second reflector is concave hemispherical.

14. The method as recited in claim 1 wherein the second reflector is concave paraboloidal.

15. The method as recited in claim 1 wherein the first reflector is convex dome-shaped.

16. The method as recited in claim 1 wherein the first reflector is concave dome-shaped.

17. The method as recited in claim 1 wherein the first reflector is a flat mirror.

18. The method as recited in claim 1 wherein the first reflector is a collimator.

19. The method as recited in claim 1 wherein step (e) comprises measuring the reflected radiation rays using an imaging detector which transforms the reflected radiation rays into a two-dimensional image.

20. The method as recited in claim 1 wherein step (e) comprises measuring the reflected radiation rays using a focal plane array which transforms the reflected radiation rays into a two-dimensional image.

21. The method as recited in claim 1 wherein step (e) comprises measuring the reflected radiation rays using a raster scanning device which transforms the reflected radiation rays into a two-dimensional image.

22. An imaging scatterometer for measuring directional energy distribution of radiation reflected from a surface of a sample material as two-dimensional images, the images being representative of surface characteristics of the sample material, as viewed from a plurality of different directions, without moving the sample material being examined, the imaging scatterometer comprising:

(a) a radiation source for producing a radiation beam directed along an optical path from the source of radiation to a selected point on the surface of the sample material;

(b) a first reflector located along the optical path, the first reflector having a surface struck by the radiation beam at a first incident point and reflecting the radiation beam to a second reflector;

(c) said second reflector located along the optical path, downstream from the first reflector, for focusing the reflected radiation beam onto the selected point on the surface of the sample material at an angle of incidence, the value of said angle of incidence being determined by the location of the first incident point on the surface of the first reflector, whereupon the sample material reflects the focused radiation beam as a plurality of reflected radiation rays;

(d) a detector for capturing the reflected radiation rays; and (e) a beam steerer located along the optical path, between the radiation source and the first reflector, for varying the location of the first incident point along the surface of the first reflector, thereby indirectly regulating the angle of incidence so as to facilitate reflectance measurements at different values of the angle of incidence.

23. The imaging scatterometer as recited in claim 22 wherein the first reflector and the second reflector have complementary shapes such that a radiation beam striking at a first incident point along the surface of the first reflector is thereafter reflected by the second reflector to strike at a substantially fixed point on the surface of the sample material at an angle of incidence, the value of the angle of incidence being determined as a result of the location of the first incident point along the surface of the first reflector.

24. The imaging scatterometer as recited in claim 22 wherein the beam steerer is a spatial light modulator for optically processing the radiation.

25. The imaging scatterometer as recited in claim 22 further comprises a beam splitter for directing the radiation beam emerging from the beam steerer onto the first incident point on the surface of the first reflector.

26. The imaging scatterometer as recited in claim 22 wherein the second reflector is concave prolate ellipsoidal.

27. The imaging scatterometer as recited in claim 22 wherein the second reflector is concave oblate ellipsoidal.

28. The imaging scatterometer as recited in claim 22 wherein the second reflector is concave hemispherical.

29. The imaging scatterometer as recited in claim 22 wherein the second reflector is concave paraboloidal.

30. The imaging scatterometer as recited in claim 22 wherein the first reflector is convex dome-shaped.

31. The imaging scatterometer as recited in claim 22 wherein the first reflector is concave dome-shaped.

32. The imaging scatterometer as recited in claim 22 wherein the first reflector is a flat mirror.

33. The imaging scatterometer as recited in claim 22 wherein the first reflector is a collimator.

34. The imaging scatterometer as recited in claim 22 wherein the detector is an imaging detector for transforming the reflected radiation rays into a two-dimensional image.

35. The imaging scatterometer as recited in claim 22 wherein the detector is a focal plane array which transforms the reflected radiation rays into a two-dimensional image.

36. The imaging scatterometer as recited in claim 22 wherein the detector is a raster scanning device which transforms the reflected radiation rays into a two-dimensional image.

* * * * *